United States Patent [19]
Kneller

[11] Patent Number: 5,322,934
[45] Date of Patent: Jun. 21, 1994

[54] PURIFICATION OF A CRUDE MRI AGENT USING CONTINUOUS DEIONIZATION

[75] Inventor: Mills T. Kneller, University City, Mo.

[73] Assignee: Mallinckrodt Medical, Inc., St. Louis, Mo.

[21] Appl. No.: 940,270

[22] Filed: Sep. 2, 1992

Related U.S. Application Data

[62] Division of Ser. No. 765,605, Sep. 25, 1991, Pat. No. 5,210,300.

[51] Int. Cl.⁵ ................................. C07F 5/00
[52] U.S. Cl. ...................................... 534/16; 534/15; 556/1; 128/653.2; 436/173; 424/5; 564/153
[58] Field of Search ............. 534/15, 16; 556/1; 564/153; 128/653.2; 424/5; 436/173

[56] References Cited

U.S. PATENT DOCUMENTS 4,826,673  5/1989  Dean et al. ........................ 534/15

OTHER PUBLICATIONS

Tangents, Issue 6, Jun. 1991, pp. 1-6 (Millipore Process System Division).

*Primary Examiner*—Shailendra Kumar
*Attorney, Agent, or Firm*—Rita D. Vacca

[57] ABSTRACT

The use of continuous deionization as an alternative or substitute method for the purification of a crude magnetic resonate.

4 Claims, 1 Drawing Sheet

PURIFICATION OF A CRUDE MRI AGENT USING CONTINUOUS DEIONIZATION

This is a division of application Ser. No. 07/765,605 filed Sept. 25, 1991, now U.S. Pat. No. 5,210,300.

FIELD OF THE INVENTION

The present invention relates the use of continuous deionization as an alternative or substitute method for purification of a crude contrast agent, and more particularly, to an improved method of purifying Ioversol by removing acids and other impurities present in the crude form thereof.

BACKGROUND OF THE INVENTION

Ioversol is disclosed as a useful nonionic X-ray contrast agent in U.S. Pat. No. 4,396,598, incorporated herein by reference. N,N'-bis(2,3-dihydroxypropyl)-5-[N(2-hydroxyethyl) glycolamido]-2,4,6-triiodoisophthalamide, more commonly called Ioversol has the following structure:

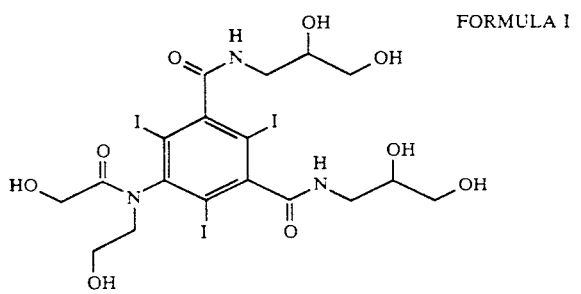

FORMULA 1

In the production of Ioversol, purification columns are used to remove impurities from the crude Ioversol product following completion of the synthetic steps as described in U.S. Pat. No. 4,396,598. Approximately 11 per cent of the crude Ioversol produced is lost from the time it enters the purification plant to the final purification of the product. Besides this large loss of Ioversol during purification, the cost and time involved in the purification operations, such as regenerating and replacing the purification columns is significant. Large amounts of costly resins and large volumes of solutions are also necessary to regenerate the purification columns between uses. These costs are significant in the production of Ioversol.

An improved procedure which eliminates the need for costly purification columns to remove impurities from the crude Ioversol product following synthesis thereof is desired as an alternate and/or a more cost efficient method of producing Ioversol. It is, therefore, an object of the present invention to meet these needs.

Additional objects and features of the present invention will appear from the following description in which the preferred methods are set forth in detail in conjunction with the accompanying drawing.

FIG. 1 is a schematic cross-sectional view of a continuous deionization system.

SUMMARY OF THE INVENTION

The present invention is a method of purifying crude Ioversol, without the costly use of purification columns, by using continuous deionization to remove a variety of impurities therefrom. Continuous deionization works like a mixed-bed resin deionizer to purify nonionic process streams while greatly reducing the amount of product customarily lost through absorption by the resin portion of the chromatography columns. This method of purifying Ioversol significantly reduces operating costs since no resin regeneration is required. Additionally, no waste streams are produced as with the regeneration of purification columns. Continuous deionization can be extended beyond currently known uses and used to remove organic and inorganic acids and/or bases and iodinated impurities from a nonionic radio-opaque process stream such as in the production of Ioversol. Impurities which may be so removed include weakly acidic and weakly basic impurities in addition to organic and inorganic acids from neutrally charged magnetic resonance imaging (MRI) agent process streams. Continuous deionization can be used to remove strong acids such as sulfuric acid, weak acids such as acetic acid in addition to the removing organic acid died impurities of 5-acetamido-N,N'-bis(2,3-dihydroxypropyl)-2,4,6-triiodoisophthalamide and N,N'-bis(2,3-dihydroxypropyl)-5-glycolamido-2,4,6-triiodoisoPhthalamide from the crude Ioversol product process stream. Continuous deionization can also be used to remove intermediate impurities including the tri-iodinated, half-acid, half-amide 5-amino-N,(2,3-dihydroxypropyl)-2,4,6-triiodoisophthalamic acid from the 5-amino-N,N'-bis (2,3-dihydroxpropyl)-2,4,6-triiodoisophthalamide process stream. 5-amino-N,N'-bis(2,3-dihydroxypropyl)-2,4,6-triiodisophthalamide is a valuable intermediate used to make Ioversol. Some of the 5-amino-N, N'-bis(2,3-dihydroxypropyl)-2,4,6-triiodoisophthalamide remains in the iodination liquor because of the presence of manufacturing impurities such as 5-amino-N(2,3-dihydroxypropyl)2,4,6-triiodoisophthalamic acid, 3-amino-1,2-propanediol, HC1, $H_2SO_4$, $Na_2SO_4$, $Na_3PO_4$, NaC1, $Na_2SO_3$ and $NaHSO_3$. Continuous deionization likewise removes organic and inorganic impurities, including acid, from crude MRI agents such as for example {[N,N''-bis[(2-methoxyethyl)amino)carbamoylmethyl]-diethylenetriamine-N,N', N'''-triaceto) gadolinium (III) process streams.

An alternate method of purification for crude agents such as those just described is greatly needed to reduce the cost of producing such agents. Continuous deionization fulfills that need by reducing the amount of product lost during purification and reducing operational costs through the elimination of the need for resin regeneration.

DETAILED DESCRIPTION OF THE INVENTION

Figure 1:
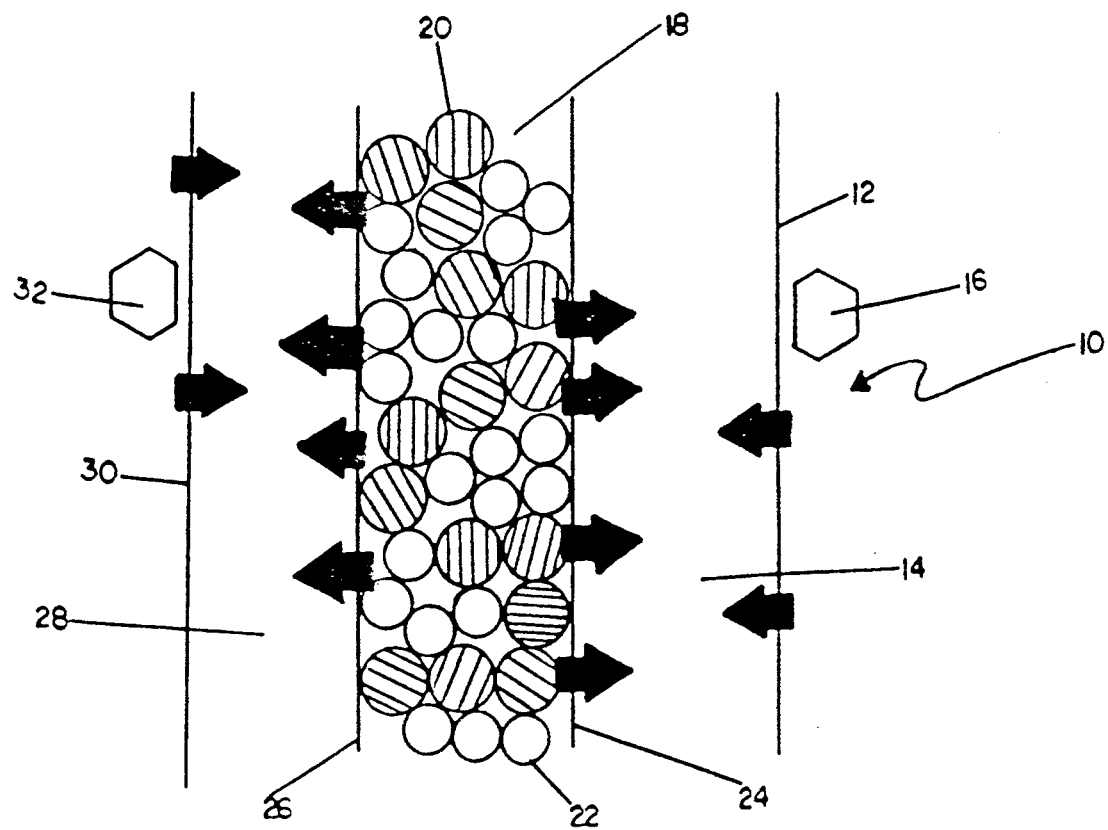

Crude Ioversol once produced must be purified prior to its use as a X-ray contrast agent. Currently, purification columns are used for this purpose. However, continuous deionization may be used as a separation technology to remove, acids and other impurities from the crude Ioversol through the use of resins similar to those used in common purification columns. Continuous deionization has the removal efficiency of mixed-resin bed deionization without the need for chemical regeneration between cycles. This means continuous deionization can purify product streams while lowering overall operating costs by eliminating the costly regeneration of chemicals. Continuous deionization removes acids and other impurities from crude Ioversol in accordance with the method illustrated in FIG. 1.

The continuous deionization system 10 illustrated in FIG. 1 is known to those skilled in the art for removing salt ions from water and other aqueous solutions. Continuous dionization system 10 is also capable of removing varied impurities from the crude Ioversol process stream without the need for chemical regeneration cycles which is the subject of the present invention. The crude Ioversol stream is drawn into the diluting compartment 18 which contains a mixed resin 20 and 22 designed to trap undesirable impurities. The impurities are then pumped out of the mixed resin 20 and 22, and across ion exchange membranes 24 and 26 by dc voltage.

Ion exchange membrane 24 is a cation permeable membrane which allows the passage of cations but not anions into the concentrating compartment 14. Opposite ion exchange membrane 24 is anion permeable membrane 12. The anion permeable membrane 12 allows anions but not cations to pass into the concentrating compartment 14. Likewise, ion exchange membrane 26 is an anion permeable membrane which allows passage of anions but notifications into the concentrating compartment 28 from the diluting compartment 18. Cation permeable membrane 30 opposite membrane 26 allows the passage of cations but not anions into the concentrating compartment 28. The anode 32 and the cathode 16 located at opposed sides of the system together create the dc voltage which powers the ion transport across the described selectively permeable membranes. Through this process of pulling anion and cation impurities from the crude Ioversol trapped in the mixed-resin bed 20 and 22, Ioversol is purified. Purified Ioversol emerges by gravity or forced flow from the diluting compartment 18.

Each of the ion exchange membranes described act as check valves to prevent acid and other impurities from reentering the purified Ioversol. The same method holds true for the purification of a crude magnetic resonance imaging (MRI) agent. The use of mixed resins in the diluting compartment is key to the present process for two reasons. First, the mixed resin makes for impurity transfer across the membrane possible even in solutions with less than one part per million concentration of impurities. Secondly, the use of mixed resins prevents H+ and OH− ions from producing localized pH shifts even at low solution conductivities. The benefits of the present method to purify nonionic X-ray contrast agents and MRI agents through continuous deionization is that the method is extremely efficient, resulting in low operating and production costs. Additionally, electrical power consumption is minimal and continuous operation of the system reduces labor costs. The present invention for the improved method of removing impurities from nonionic X-ray contrast agents such as Ioversol or neutrally charged MRI agents through the continuous deionization process is further illustrated by the following examples, but is not intended to be limited thereby.

EXAMPLE 1

Purification of Crude Ioversol Using Continuous Deionization

A crude solution of Ioversol containing 1 to 25% weight per volume Ioversol, small amounts of N,N'-bis(2,3-dihydroxypropyl)-5-glycolamido-2,4,6-triiodoisophthalamide, 5-acetamid-N,N'-bis(2,3-dihydroxypropyl)-2,4,6-triiodoisophthalamide, 5-amino-N,N'-bis(2,3-dihydroxpropyl)-2,4,6-triiodoisophthalamide, and N,N'-bis(2,3-dihydroxypropyl)-5-[N(2-hydroxyethyl) acetamido]-2,4,6-triiodoisophthalamide, a very small amount of N,N'-bis(2,3-dihydroxypropyl)-5-[[N-(2-hydroxyethyl)-carbamoyl]methoxy]-2,4,6-triiodoisophthalamide, about 0.07 milliequivalents/milliliter of $H_2SO_4$, and about 0.03 milliequivalents/milliliter of acetic acid is pumped through the cells of the continuous deionization system at a rate of 1 to 10 gallons per minute. The pH of the crude Ioversol solution is initially ranging between a pH 1.0 to 2.0, but the pH will rise as it passes through the compartments or cells of the continuous deionization system. The continuous deionization system is operated at 2 to 7 dc volts per cell. The sulfuric acid, acetic acid, N,N'-bis(2,3-dihydroxypropyl)-5-glycolamido-2,4,6-triiodoisophthalamide, and 5-amino-N,N'-bis(2,3-dihydroxpropyl)-2,4,6-triiodoisophthalamide are nearly completely removed and some N,N'-bis (2,3-dihydroxypropyl)-5-[[N-(2-hydroxyethyl)-carbamoyl]methoxy]-2,4,6-triiodoisophthalamide and 5-acetamido-N,N'-bis(2,3-dihydroxypropyl)-2,4,6-triiodoisophthalamide triiodoisophthalamide is likewise removed.

EXAMPLE 2

Purification of crude {[N,N''-bis}(2-methoxyethyl)amino) carbamoyl-methyl]diethylenetriamine-N,N'N''-triaceto) gadolinium (III) Using Continuous Deionization A crude solution of the neutral MRI agent ([N,N''-bis[(2-methoxyethyl)amino) carbamoyl-methyl]diethylenetriamine-N,N'N ''-triaceto) gadolinium (III) hereinafter called MEAGdDTPA, containing 2 to 30% weight per volume MEAGdDTPA, small amounts of gadolinium diethylenetriamine pentaacetic acid (GdDTPA), monomethoxyethylamide, and similar acidic gadolinium complexes which are impurities arising from the MEAGdDTPA manufacture is pumped through the compartments or cells of the continuous deionization system at a rate 1 to 20 gallons per minute. The pH of the crude MEAGdDTPA solution will rise as it passes through the cell of the continuous deionization system. The continuous deionization system is operated at 2 to 7 dc volts per cell. All impurity components are nearly completely removed.

EXAMPLE 3

Removal of Salts and Acids From 5-amino-N,N'-bis-(2.3 dihydroxypropyl)-2,4,6-triiodoisophthalamide production Waste Stream Using Continuous Deionization This example process of the present invention, as with the previous examples given, is less expensive, easier to perform and results in fewer impurities than currently used processes.

The waste stream from 5-amino--N,N'-bis-(2,3 dihydroxypropyl)-2,4,6-triiodoisophthalamide manufacture containing 1 to 20 percent weight per volume 5-amino--N,N'-bis-(2,3 dihydroxypropyl)-2,4,6-triiodoisophthalamide is filtered to remove salts and is then pumped through the cells of the continuous deionization system at a rate of 1 to 20 gallons per minute. The pH of the solution is initially about 1 to 5 but rises as it passes through the cell of the continuous deionization system. The continuous deionization system is operated at 2 to 7 volts dc per cell. Nearly all the HCl, $H_2SO_4$, $NaHSO_3$, $Na_2SO_4$, $Na_3PO_4$, NaCl, $Na_2SO_4$, 5-amino-N(2,3-dihydroxypropyl) 2,4,6-triiodoisophthalamic acid and 3-amino-1,2-propanediol are removed. The waste stream that has been purified by the continuous deionization system is concentrated to cause the crystallization of 5-amino-N,N'-bis-(2,3 dihydroxypropyl)-2,4,6-triiodoisophthalamide. The 5-amino-N,N'-bis--(2,3 dihydroxypropyl)-2,4,6-triiodoisophthalamide is then collected, dried and used in the manufacture of Ioversol.

The improved method of purification for nonionic X-ray contrast and FLRI agents of the present invention is less expensive, easier to perform and results in significantly fewer impurities than currently used processes.

Accordingly, having described my invention I claim:

1. A method for the purification of a nonionic gadolinium containing crude magnetic resonance imaging agent comprising the steps of:
   a) passing said nonionic crude magnetic resonance imaging agent through a mixed-resin bed contained between a cation permeable membrane which allows the passage of cations and not anions and an anion permeable membrane which allows the passage of anions and not cations; and
   b) applying an electrical current to said cation permeable membrane and anion permeable membrane; whereby impurities are pumped through said cation permeable membrane and anion permeable membrane to purify said magnetic resonance imaging agent.

2. The method of purification according to claim 1 wherein said magnetic resonance imaging agent is {[5-N,N'-bis](2-methoxyethyl)amino)carbamoyl-methyl]-diethylenetriamine-N,N',N'''-traiceto)gadolinium (III).

3. The method of purification according to claim 1 wherein said electrical current is a dc current.

4. The process of purification according to claim 1 wherein said impurities are selected from the group consisting of gadolinium diethylenetriamine pentaacetic acid, gadolinium diethylenetriamine pentaacetic acid monomethoxyethylamide, and similar acidic gadolinium complexes.

* * * * *